(12) United States Patent
Gartside et al.

(10) Patent No.: US 6,777,582 B2
(45) Date of Patent: Aug. 17, 2004

(54) PROCESS FOR PRODUCING PROPYLENE AND HEXENE FROM C4 OLEFIN STREAMS

(75) Inventors: Robert J. Gartside, Summit, NJ (US); Marvin I. Greene, Wayne, NJ (US); Quincy J. Jones, Belleville, NJ (US)

(73) Assignee: ABB Lummus Global Inc., Bloomfield, NJ (US)

( * ) Notice: Subject to any disclaimer, the term of this patent is extended or adjusted under 35 U.S.C. 154(b) by 0 days.

(21) Appl. No.: 10/093,322

(22) Filed: Mar. 7, 2002

(65) Prior Publication Data

US 2003/0176754 A1 Sep. 18, 2003

(51) Int. Cl.[7] .............................................. C07C 6/04
(52) U.S. Cl. .................. 585/324; 585/330; 585/643; 585/646; 585/647
(58) Field of Search ............................... 585/324, 330, 585/643, 646, 647

(56) References Cited

U.S. PATENT DOCUMENTS

| | | | |
|---|---|---|---|
| 3,526,676 A | 9/1970 | Turner et al. | 260/683 |
| 4,814,542 A * | 3/1989 | Forlani et al. | 585/666 |
| 5,043,520 A | 8/1991 | Hamilton, Jr. | 585/646 |
| 5,057,638 A * | 10/1991 | Sweeney | 585/324 |
| 5,698,760 A | 12/1997 | Kelly | 585/643 |
| 6,075,173 A | 6/2000 | Chodorge et al. | 585/324 |
| 6,159,433 A | 12/2000 | Chodorge et al. | 422/189 |
| 6,166,279 A | 12/2000 | Schwab et al. | 585/324 |
| 6,538,168 B1 * | 3/2003 | Schwab et al. | 585/647 |
| 2001/0003140 A1 | 6/2001 | Schwab et al. | 585/644 |

FOREIGN PATENT DOCUMENTS

| | | |
|---|---|---|
| DE | 197 46 040 A1 | 4/1999 |
| EP | 0 832 867 A1 | 9/1997 |
| WO | WO 00/14038 | 3/2000 |

OTHER PUBLICATIONS

Banks, Robert L., "Catalytic Disproportionation of Olefins", American Chemical Society, New York Meeting, Aug. 27–Sep. 1, 1972.

* cited by examiner

Primary Examiner—Thuan D Dang
(74) Attorney, Agent, or Firm—Alix, Yale & Ristas, LLP

(57) ABSTRACT

A $C_3$ to $C_6$ hydrogen cut from a cracking unit is processed for the conversion of olefins to propylene and hexene via autometathesis. The autometathesis of a mixed normal butenes feed in the presence of a metathesis catalyst operates without any ethylene in the feed mix to the metathesis reactor. Some fraction of the 2-butene feed may be isomerized to 1-butene and the 1-butene formed plus the 1-butene in the feed react rapidly with the 2-butene to form propylene and 2-pentene. The feed to the reactor also includes the recycle of the 2-pentene formed in the reactor with unreacted butenes to simultaneously form additional propylene and hexene. In one embodiment, some or all of the 3-hexene formed in the reaction is isomerized to 1-hexene. In another embodiment, some portion of the 3-hexene produced in the main metathesis reaction is reacted with ethylene to produce 1-butene without the need for superfractionation. In another embodiment, the 3-hexene product is hydrogenated and recycled back to the cracking heaters.

44 Claims, 6 Drawing Sheets

PROCESS FOR PRODUCING PROPYLENE AND HEXENE FROM C4 OLEFIN STREAMS

BACKGROUND OF THE INVENTION

The present invention relates to the processing of a $C_3$ to $C_6$ hydrocarbon cut from a cracking process, such as steam or fluid catalytic cracking, primarily for conversion of $C_4$ and $C_5$ olefins to propylene via auto-metathesis.

In typical olefin plants, there is a front-end demethanizer for the removal of methane and hydrogen followed by a deethanizer for the removal of ethane, ethylene and $C_2$ acetylene. The bottoms from this deethanizer tower consist of a mixture of compounds ranging in carbon number from $C_3$ to $C_6$. This mixture is separated into different carbon numbers typically by fractionation.

The $C_3$ cut, primarily propylene, is removed as product and is ultimately used for the production of polypropylene or for chemical synthesis such as propylene oxide, cumene, or acrylonitrile. The methyl acetylene and propadiene (MAPD) impurities must be removed either by fractionation or hydrogenation. Hydrogenation is preferred since some of these highly unsaturated $C_3$ compounds end up as propylene thereby increasing the yield.

The $C_4$ cut consisting of $C_4$ acetylenes, butadiene, iso and normal butenes, and iso and normal butane can be processed in many ways. A typical steam cracker $C_4$ cut contains the following components in weight %:

| | |
|---|---|
| $C_4$ acetylenes | trace |
| butadiene | 33% |
| 1-butene | 15% |
| 2-butene | 9% |
| isobutene | 30% |
| iso & normal butane | 13% |

Conventionally, it is common for some of the products of the stream to be separated and the balance recycled back to the olefins unit for pyrolysis or sent offsite as an olefinnic product. The $C_4$ acetylenes are first removed by selective hydrogenation followed by butadiene extraction. Alternately they are hydrogenated along with butadiene to form butenes. Isobutene can be removed by fractionation, by reaction to methyl tertiary butyl ether using methanol, or by reaction with itself and normal butenes in a catalytic $C_4$ dimerization unit. If the stream is to be recycle cracked, the butenes are further hydrogenated to butanes. An alternative processing option is metathesis. As practiced commercially in several units, conventional metathesis involves the reaction of normal butenes with ethylene to form propylene. The isobutene is typically removed before metathesis with ethylene. Isobutene does not react with ethylene or 2 butene under metathesis conditions. Thus isobutene will build up in the system as the $C_4$ fraction is recycled to obtain higher conversions. Isobutylene does however react with product propylene to form ethylene and 2 methyl-2-butene. In many cases this is not desired since it reduces propylene production. Typically after butadiene hydrogenation to normal butenes, over 50% of this stream is linear olefins.

The bottoms from the isobutene fractionation containing primarily the 1-butene and 2-butene are mixed with excess ethylene and passed through the metathesis or olefin conversion reacting step. In this conversion reaction step, the primary reaction is:

2-butene+ethylene→2 propylene

The unconverted butenes from the reaction are recycled to obtain a net high conversion of the butenes to propylene.

Typical molar ratios of ethylene/butenes are 1.5 or higher for metathesis with ethylene. Excess ethylene reduces the potential for the butenes to react with themselves thereby reducing the selectivity for propylene formation. The theoretical minimum ethylene required for maximum propylene is 1 mol/mol of 2-butene. The high concentrations of ethylene minimize the non-selective, in terms of propylene, reactions of the butenes with themselves by auto-metathesis. These reactions are shown below:

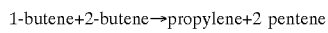
1-butene+2-butene→propylene+2 pentene

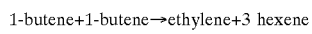
1-butene+1-butene→ethylene+3 hexene

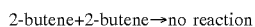
2-butene+2-butene→no reaction

As can be seen, instead of 1 mol of butenes forming 1 mol of propylene and 1 mol of ethylene forming the other mol of propylene, in these auto-metathesis reactions, 2 mols of butene form less than 1 mol of propylene. In spite of the lower selectivity to propylene, this may be an economically desirable route dependent upon the relative values of feeds and products since ethylene is historically higher valued than propylene or butenes. Note however, when the metathesis reaction utilizes ethylene as a co-feedstock, the product of the $C_5$ and $C_6$ normal olefins are reduced.

The $C_5$ and heavier stream from the steam cracker is typically used in the production of gasoline but sometimes the $C_5$'s are separated and recycled to the cracking heaters. A typical steam cracker $C_5$ stream contains the following components in weight %:

| | |
|---|---|
| pentanes | 40% |
| 1-pentene | 5% |
| 2-pentene | 5% |
| isopentene | 7% |
| cyclopentene | 3% |
| cyclopentadiene | 18% |
| n-pentadienes | 8% |
| Isoprene | 14% |

This $C_5$ stream contains considerably lower amounts of linear components than the $C_4$ stream. After n-pentadiene hydrogenation, only about 20% of this stream is linear olefins. If the n-pentenes are processed through metathesis, the reactions are:

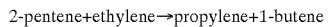
2-pentene+ethylene→propylene+1-butene

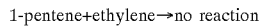
1-pentene+ethylene→no reaction

The $C_5$ stream and the $C_6$ stream are conventionally sent as a bottom product from a fractionation tower to gasoline. In some cases, after hydrogenation, the $C_5$ stream separated by fractionation and is recycled back to the cracking heaters. The $C_6$+ stream after $C_5$ separation is typically sent to gasoline blending since it contains higher octane value aromatics such as benzene in addition to non-aromatic compounds.

For metathesis reactions, the catalyst is typically an oxide of Group VI B or Group VII B metals supported on either alumina or silica supports. In some cases, this oxide is physically admixed with a double bond isomerization catalyst such as MgO. In the reactor, the 2-butene and ethylene are metathesised to propylene. The 1-butene does not react with ethylene. The isomerization catalytic activity incorporated allows 1-butene to be isomerized to 2-butene which is then reacted with the ethylene. The effluent containing propylene, unreacted ethylene and butenes and some $C_5$ and heavier products is first passed through a deethylenizer for removal of that unreacted ethylene and then to a depropylenizer where product propylene is removed overhead. The bottoms may be sent to a debutylenizer where unreacted $C_4$s are recovered and recycled. The $C_5$ and heavier fraction is typically sent to gasoline blending. Alternately, a $C_4$ stream is withdrawn from the depropyleneizer above the bottoms and recycled with the net bottoms of $C_5$ and heavier again being sent to gasoline blending.

In the conventional process for the metathesis of butenes to propylene such as generally described above, there are several problems or disadvantages. First, the reaction takes place with ethylene which not only consumes a valuable olefin but requires recovery for the excess using energy intensive refrigeration systems and then recirculation requiring compression. Secondly, to prepare the feed, there is a separate fixed bed hydrogenation units for butadiene. In the butadiene hydrogenation step, if high 2-butene concentrations are desired, additional hydrogenation is specified in order to maximize the hydroisomerization of 1-butene to 2-butene. High 2-butene concentration is desired because the reaction of 1-butene with ethylene will not occur and thus the 1-butene must be isomerized to 2-butene within the reaction bed itself by a double bond isomerization catalyst such as MgO. In the hydroisomerization of 1-butene to 2-butene in the selective butadiene hydrogenation unit, there is a substantial loss (10+%) of butenes to paraffins due to the added hydrogen which represents a considerable feed loss to the metathesis conversion step. Further, if fractionation is employed for the isobutene removal step, there is an additional loss of butenes since 1-butene is difficult to separate from isobutene without a very expensive fractionation tower.

In the prior U.S. patent application Ser. No. 09/769,871 filed Jan. 25, 2001, an improved process is disclosed and claimed for the processing of the $C_3$ to $C_6$ cut from a cracking process to produce an essentially pure 2-butene stream for the feed to the metathesis reaction process for reaction with ethylene. That improved process involves the use of a catalytic hydroisomerization de-isobutyleneizer tower. In that prior patent application, the metathesis is the typical reaction of 2-butene and ethylene to produce propylene.

Although the yield of propylene is relatively high when utilizing excess ethylene as a reactant, the production of propylene from the cracking cut without the use of ethylene would be desirable, such as when the supply of ethylene is tight and/or ethylene is expensive, even though the selectivity of butenes to propylene is dramatically reduced as long as the increased other products can be used advantageously.

As a part of the background of the present invention, several prior patents are relevant. The Schwab et al U.S. Pat. No. 6,166,279 discloses a process for producing propylene from cracked $C_4$ streams using a two-step process. The first step uses the reaction of 1-butene with 2-butene to form propylene and 2-pentene. In a separate reaction step, 2-pentene is reacted with ethylene to form additional propylene and 1-butene. The 1-butene formed is then isomerized in a third reaction step and recycled to the first reactor as an isomerization mixture of 1 and 2-butene. On a purely theoretical basis, the reactions are:

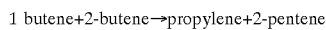  step 1:

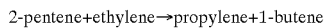  step 2:

The net reaction of these two steps is:

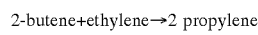

This is identical to the base metathesis reaction. The preferred feed mixture is a mix of 1-butene and 2-butene where the 1-butene is in excess. This is achieved by choice of feedstock composition and by recycling the 1-butene produced in step 2. Under these conditions, some reaction between two 1-butene molecules will result in the formation of ethylene and 3-hexene. This formation of ethylene from butenes shifts the overall selectivity of the net reaction such that on a fresh feed basis, less ethylene and more butenes are required per unit of propylene.

U.S. Patent Application Publication US2001/0003140 A1 discloses separately the second step above, namely the reaction of 2-pentene with ethylene to form propylene and 1-butene. Similarly, U.S. Pat. No. 5,698,760 discloses a process where a mixed pentene stream is reacted with ethylene under metathesis conditions to form butenes and propylene. U.S. Pat. No. 6,159,433 and U.S. Pat. No. 6,075,173 disclose processes for reacting steam cracker $C_4$'s consisting of reacting the butenes streams with ethylene to form primarily propylene.

U.S. Pat. No. 5,043,520 discloses a process where olefins ranging from C2 to C100 are contacted with a metathesis catalyst physically admixed with an acidic zeolitic double bond isomerization catalyst. The concept of using a physically admixed double bond isomerization catalyst has been well known. In the preprints of the Symposium on Hydrocarbon Chemistry, Division of Petroleum Chemistry, September, 1972 American Chemical Society meeting, R. L. Banks of Phillips Petroleum states, "High selectivity to primary disproportionation products is desirable for many applications and this can be achieved by reducing double bond isomerization activity of catalysts. However, for certain applications, such as processing detergent range linear olefins from propylene, high double bond activity is essential; symmetrical olefins such as 2-butene produced from the disproportionation of propylene, will not disproportionate and a shift in location of the double-bond is needed prior to the disproportionation reaction. Incorporation of acid-type double bond isomerization catalysts in the system would also promote skeletal isomerization and dimerization, resulting in branched products. Magnesium oxide is also a very selective catalyst for double bond isomerization and is compatible with tungsten oxide catalyst."

Alpha olefins are important co-monomers in the production of both polyethylene and polypropylene. In U.S. patent application Ser. No. 09/863,973, which is incorporated herein by reference, a process for producing a catalyst and a process for the isomerization of internal olefins to alpha olefins is disclosed. In one example, a mixed n-butenes stream consisting of 1-butene and 2-butene after removal of isobutene is passed through a combined isomerization/fractionation step to produce essentially pure 1-butene as an overhead product from the fractionator and a bottoms stream consisting of essentially pure 2-butene. The 2-butene stream can either be sent to product or recycled through the isomerization step to form more 1-butene. Similarly 3-hexene can be isomerized and fractionated to produce 1-hexene.

The separation of closely boiling olefin isomers is quite difficult. This is usually done in super-fractionators employing many fractionation stages and extremely high reflux ratios. Further, even at high temperatures, the equilibrium concentration of the alpha olefin is low compared to the other isomers. For a mixed $C_4$ stream, at 650° F. reaction temperature, the 1-butene content at equilibrium is 22% with the balance being 2-butene. For the hexene stream, the concentration of 1-hexene at 650° F. is 8% with the balance being 2 and 3-hexene. In a process to isomerize and then fractionate a mixed olefin stream to recover high purity alpha olefins, the relative volatility between isomers is very close such that high reflux ratios and large number of separation stages are required. Also with the feed mixture at low concentration, high recycle through the isomerization section is required which increases the tower cost and energy requirements even further. If an alternate route could be achieved that avoided the extensive recycle and super-fractionation for the production of alpha olefins, there would be considerable economic benefit.

SUMMARY OF THE INVENTION

The object of the present invention is to provide an improved process for the conversion of olefins for the production of propylene from a $C_4$ cut from a steam or other cracking process. The invention involves the auto-metathesis of a mixed normal butenes feed in the presence of a metathesis catalyst and specifically operates without any ethylene in the feed mix to the $C_4$ metathesis unit. Some fraction of the 2-butene feed may be isomerized to 1-butene and the 1-butene formed plus the 1-butene in the feed react rapidly with the 2-butene to form propylene and 2-pentene. The feed to the reactor also includes the recycle of the 2-pentene formed in the reactor with unreacted butenes to simultaneously form additional propylene and hexene. In one embodiment, some or all of the 3-hexene formed in the reaction is isomerized to 1-hexene. In another embodiment, some portion of the 3-hexene produced in the main metathesis reaction is reacted with ethylene to produce 1-butene without the need for super-fractionation. In another embodiment, the 3-hexene product is hydrogenated and recycled back to the cracking heaters.

In a further embodiment, the preparation of the feed for the metathesis reaction from steam cracker $C_4$'s involves a system using catalytic distillation hydrogenation to maximize the 2-butene content while simultaneously removing the isobutylene in the $C_4$ stream.

DESCRIPTION OF THE PREFERRED EMBODIMENT

Figure 1:
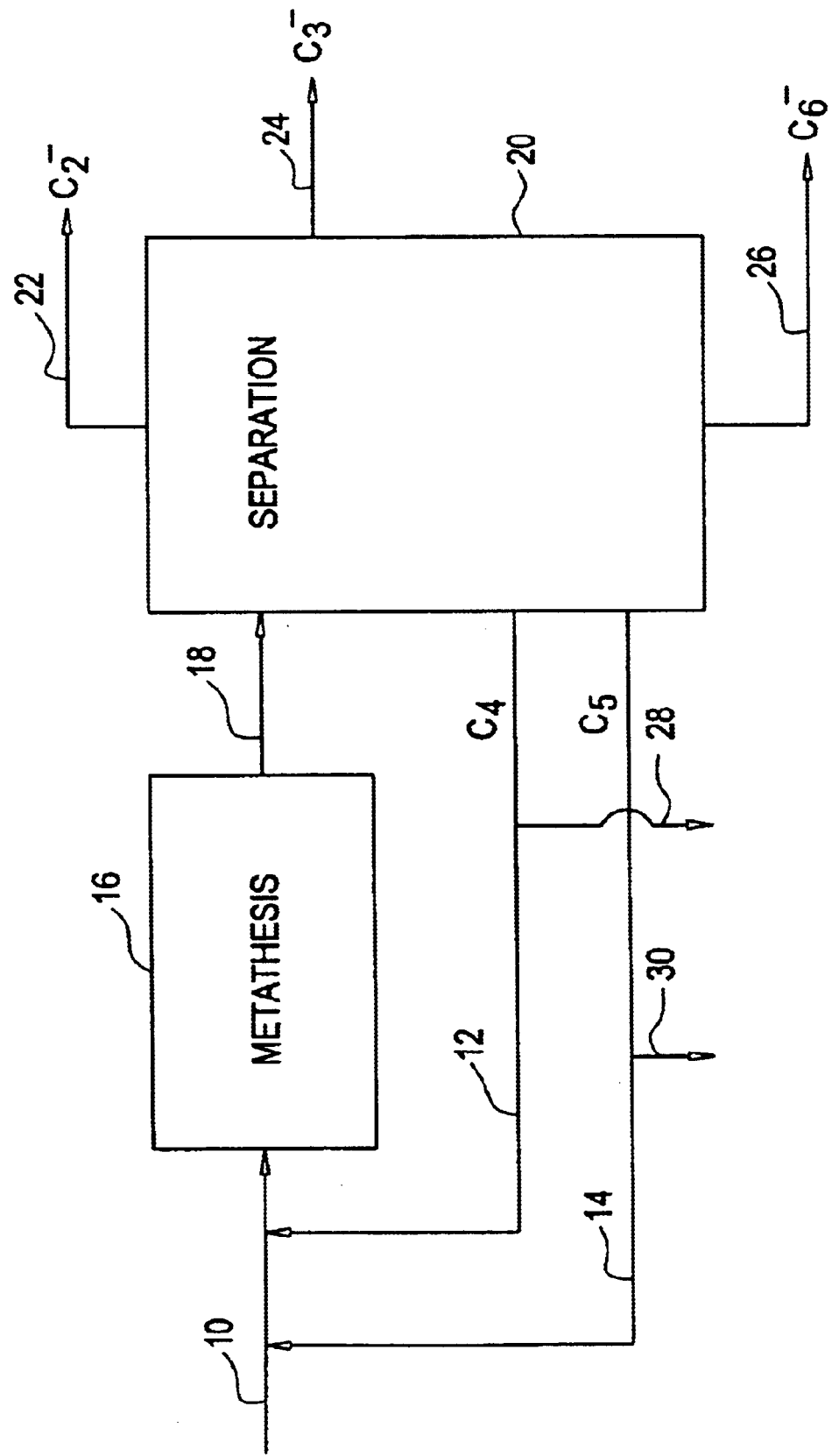
FIG. 1 is a flow diagram of the process according to the present invention.

The present invention involves the auto-metathesis of an essentially pure normal butene stream. The normal butene stream is essentially pure in the sense that it contains the linear olefins 1- and 2-butene in any proportion but does not contain any significant quantities of other olefins including isobutene. However, it could contain paraffin components which are inert in the metathesis reaction. This stream is admixed with recycle pentenes formed in the metathesis reaction. Although the auto-metathesis portion of the process will be described in detail later, it involves the rapid reaction of the 1-butene with 2-butene to form propylene and 2-pentene, the simultaneous isomerization of some fraction of the 2-butene to 1-butene and the reaction of the recycled pentene to form additional propylene and hexene. This preferred embodiment is shown in FIG. 1.

The feedstock 10 is a mix of essentially pure normal butenes. This can be any mixture of 1-butene and 2-butene and can contain $C_4$ paraffins but the amount of isobutene should not exceed 10% of the feed mixture and preferably not exceed 5% of the feed mixture and most preferably not exceed 2% of the feed mixture. This feed 10 is admixed with a recycle 12 of unreacted normal butenes as well as a recycle 14 of normal pentenes and fed to the metathesis reactor 16. This reactor 16 operates at a pressure between 2 and 40 atmospheres and preferably between 5 and 15 atmospheres. The catalyst contained within this reactor may be any known metathesis catalyst including oxides of Group VIB and Group VII B metals on supports. Catalyst supports can be of any type and could include alumina, silica, mixtures thereof, zirconia, and zeolites. In addition to the metathesis catalyst, the catalyst in reactor 16 can include a double bond isomerization catalyst such as magnesium oxide or calcium oxide. The reaction takes place at a temperature between 50° and 450° C., preferably between 300° and 400° C. The effluent 18 from the reactor 16 consists of a mixture of ethylene, propylene, unreacted butenes, pentenes (primarily 2-pentene), hexenes, and small amounts of heavier components. By limiting the extent of iso-olefins in the feed, the quantity of branched olefins in the effluent is minimized.

The effluent 18 from reactor 16 is sent to a separation system 20. This separation system consists of distillation apparatus and the effluent is separated into carbon number groups by technology well known in the art. The products of the separation system are an ethylene stream 22 comprising any ethylene that may be present, a propylene stream 24, a hexene stream 26, a butene stream 12 that is recycled to the reactor 16, and a pentene stream 14 that is also recycled to the reactor 16. Purge streams 28 and 30 are used to control the amount of recycle and the paraffin content of the recycle streams 12 and 14 to avoid overloading the reactor. The $C_4$ purge stream 28 would typically be hydrogenated and recycled to the cracking heaters as will be described later in connection with FIG. 5.

In the processes of the prior art, the recovered pentenes stream 14 would either be sent to gasoline as a product or reacted with ethylene to form additional propylene and 1-butene via the reaction:

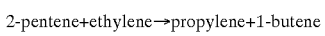
2-pentene+ethylene→propylene+1-butene

However, if it is desired to minimize or eliminate ethylene as a feedstock, then the reaction of the pentenes with ethylene would not be considered. Further, reacting the produced pentenes with ethylene adds an additional processing step. In the process of the present invention, the pentenes are recycled to the main metathesis reactor 16 where the reaction of the formed 2-pentene with 1-butene occurs according to:

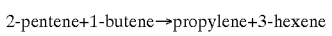
2-pentene+1-butene→propylene+3-hexene

To the extent that there is isomerization activity within the catalyst system in reactor 16, some of the 2-pentene is isomerized to 1-pentene and this can react with 2-butene according to:

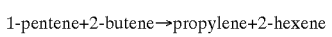
1-pentene+2-butene→propylene+2-hexene

The recycle of the pentenes stream to the metathesis reactor where there is no ethylene feed results in several major advantages:

a. The selectivity to propylene is dramatically increased. The reaction of butenes via the reaction 1 butene+2-butene→propylene+2-pentene produces 1 mol of propylene per two mols of butene reacted or a 37% weight selectivity to propylene. By adding recycle pentenes, and hence adding the reaction 2-pentene+1-butene→propylene+3-hexene, the overall net reaction becomes 2 1-butene+2-butene→2 propylene+3-hexene. This has a 50% weight selectivity to propylene.

b. The product hexene is more valuable than pentene as a co-monomer for polyethylene production (after isomerization to the alpha olefin).

c. The product hexene is also a more valuable pyrolysis feed than pentene since it produces more ethylene and propylene per unit of fuel than either pentene or butene.

d. There is no second reaction step required (reaction of pentenes and ethylene) as it is in some processes that attempt to increase propylene selectivity by processing $C_5$'s.

The following table presents an example of the shift in selectivity associated with recycling the pentenes produced in the primary reaction. Reaction for all these cases used a catalyst consisting of $WO_3$ on silica but no double bond isomerization catalyst admixed with the metathesis catalyst. The WHSV was 12 (wt butene/wt $WO_3$-hr), the temperature was 343° C. and the pressure was 5 barg.

|  | Run | | | |
| --- | --- | --- | --- | --- |
|  | 125 | 148 | 119 | 150 |
| Feed mol % | | | | |
| 1-Butene | 25 | 28 | 98 | 93 |
| 2-Butene | 75 | 50 | 0 | 0 |
| Iso-Butene | 0 | 0 | 2 | 2 |
| 2-Pentene | 0 | 20 | 0 | 5 |
| n-Butene conversion mol % | 35 | 48 | 44 | 45 |
| Selectivity mol % | | | | |
| Ethylene | 3 | 4 | 41 | 41 |
| Propylene | 48 | 51 | 7 | 9 |
| 2-Pentene | 44 | 29 | 8 | 0.6 |
| 3-Hexene | 5 | 15 | 43 | 48 |
| Heavier |  |  | 1 | 1.4 |

Run 125 is a feed with a high amount of 2-butene in the feed. When reacted with no pentene recycle, conversion is 35% with almost equal molar production of propylene and pentene by the reaction:

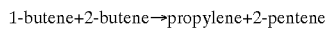

1-butene+2-butene→propylene+2-pentene

Run 148 replaced some of the 2-butene with 2-pentene to simulate recycle of this component. As can be seen, the net pentene produced decreased by 34% (44 to 29), the propylene increased by 3% and hexenes increased by a factor of 3. Significantly, the butenes conversion also increased from 35 to 48% which results in an even greater yield of propylene and hexene.

Figure 5:
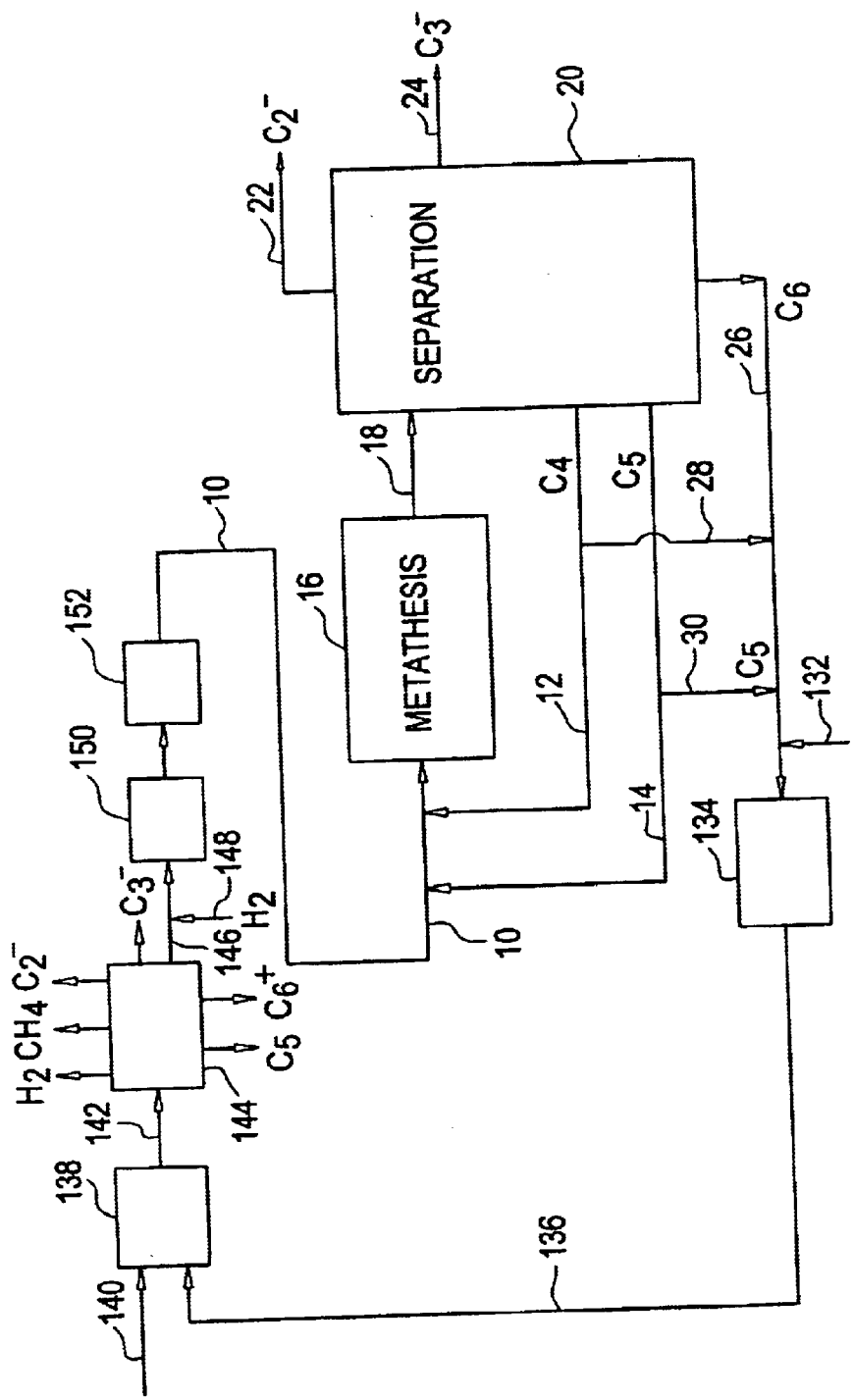
FIG. 5 is a flow diagram of an embodiment of the process shown in FIG. 1 wherein $C_5$ and $C_6$ streams are hydrogenated and recycled to the cracking process.

Run 119 represents a $C_4$ feed with essentially pure 1-butene feed. Under the same operating conditions, the conversion is about 45%. However, the selectivity of propylene, 7%, and pentene, 8%, are low reflecting the high concentration of 1-butene in the feed and the lack of any specific isomerization catalyst admixed with the metathesis catalyst. In run 150, some of the 1-butene is replaced with 2-pentene. The amount of 2-pentene is slightly less than the 2-pentene produced in the reaction of run 119. The conversion remained essentially the same. The recycle of the pentene does two things. The selectivity of both propylene and hexene are increased reflecting the reaction of 2-pentene with 1-butene. Secondly, by having 2-pentene present in the feed, the equilibrium reaction of 1-butene with 2-butene (formed by isomerization of 1-butene over the metathesis catalyst itself) is suppressed. Thus in net, no pentene is formed as a final reaction product. Optionally, some of the 2-pentene could be hydrogenated and recycled to the cracking heaters as shown in FIG. 5 to be described later. The $C_5$'s from the metathesis of $C_4$ olefins are linear and thus have a good potential for pyrolysis. $C_5$'s directly from the cracker contain only limited normal pentenes with over 80% typically being isopentenes and cyclo $C_5$ compounds.

Figure 2:
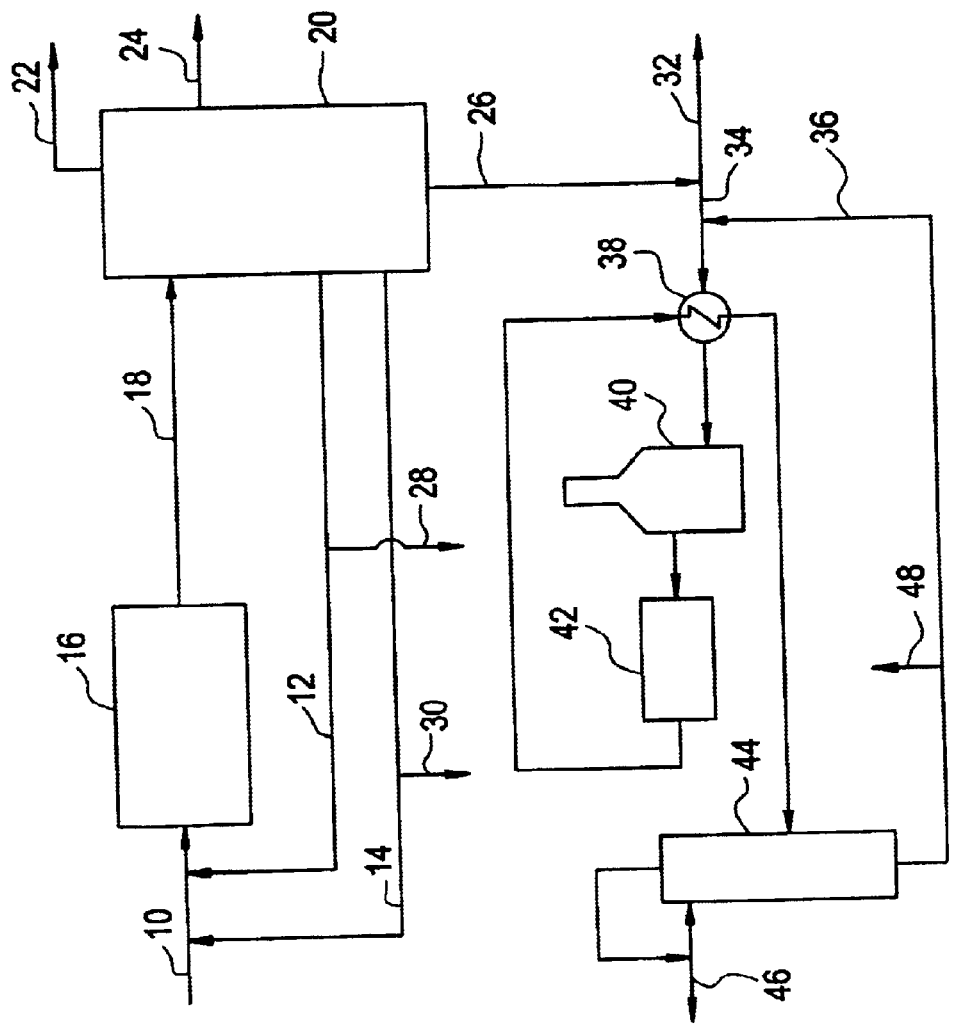
FIG. 2 is a flow diagram of the process showing one embodiment of the process.

In the embodiment of the present invention shown in FIG. 2, some or all of the hexene product 26 following the separation step 20 is sent to an isomerization reaction system where 1-hexene is produced. 1-hexene is a valuable co-monomer for polyethylene production. Effluent 26 is mostly 3-hexene resulting from the reaction of 1-butene with 2-pentene to form propylene and 3-hexene or the reaction of 1-butene with itself to form ethylene and 3-hexene. This stream 26 is split with some of the 3-hexene purged at 32 as a product and the remainder 34 being sent to the isomerization step. The stream 34 is admixed with recycle 36 and passed to a heat exchanger 38 and preheater 40 where the temperature is raised from the fractionation temperature of approximately 38° C. up to the range of 300 to 450° C. and preferrably about 345° C. Pressures can be from 1 to 20 atm and preferably 3 to 10 atm. The isomerization reactor 42 contains a double bond isomerization catalyst comprising a basic metal oxide such as MgO or CaO or mixtures thereof and preferably a high purity basic metal oxide as described in the previously mentioned U.S. patent application Ser. No. 09/863,973. Under these high temperature conditions, the 3-hexene is isomerized to a mixture of 1-,2- and 3-hexenes and passed through the heat exchanger 38 to the fractionation tower 44. The overhead 46 of tower 44 is a high purity 1-hexene stream product. The bottoms 36 of tower 44 is a mixed 2- and 3-hexene stream that is recycled back to the isomerization step for additional conversion into valuable 1-hexene. Some heavier compounds are formed in the primary metathesis reaction step 16 and subsequently additional heavier components are formed in the isomerization reaction step 42. These are removed via purge stream 48.

Figure 3:
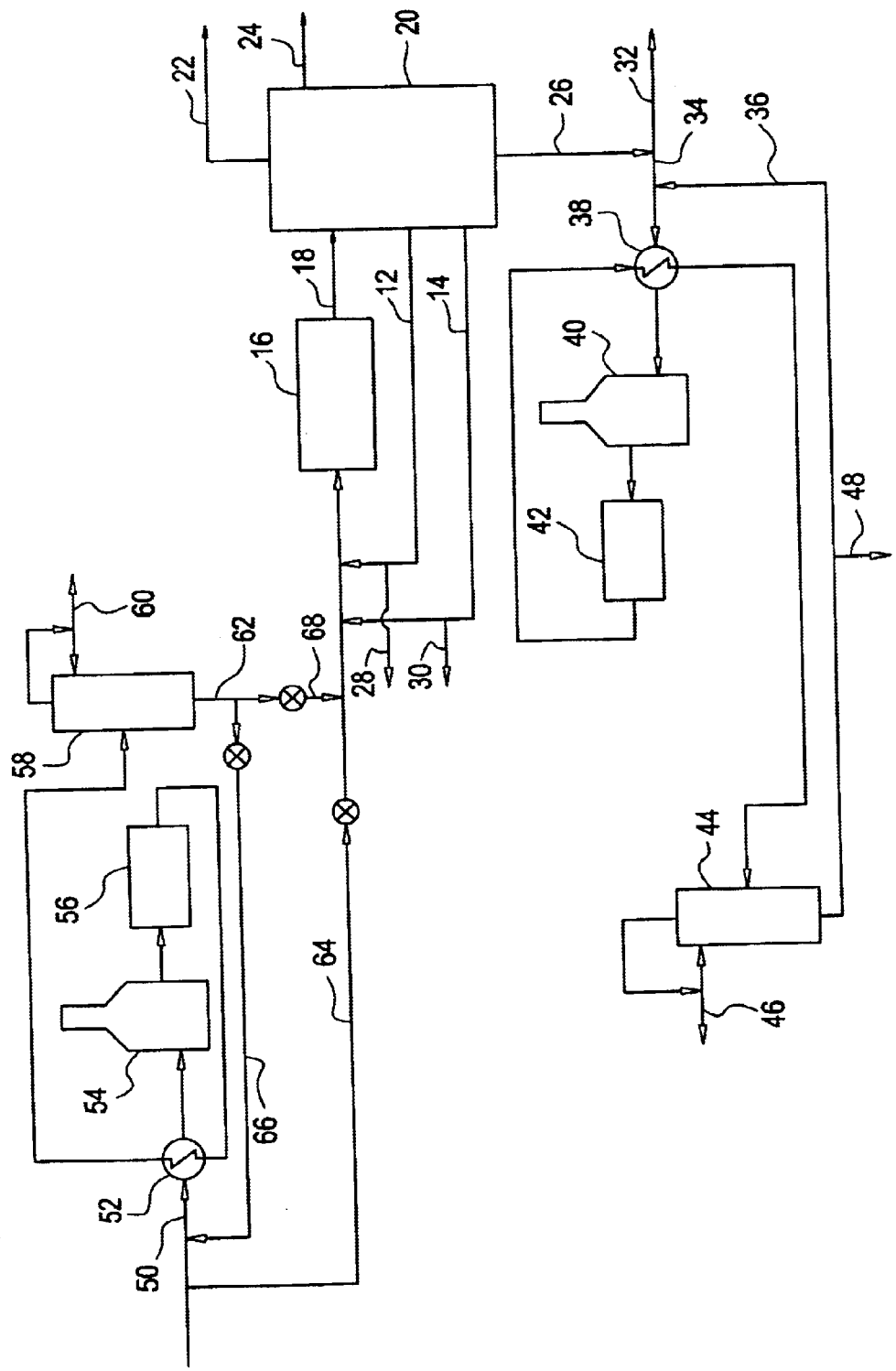
FIG. 3 is another flow diagram showing another embodiment of the process with co-production of 1-butene via feedstock isomerization.

The embodiment of the invention shown in FIG. 3 is for the co-production of propylene, 1-butene and 1-hexene. Since both 1-butene and 1-hexene are important co-monomers for linear low density polyethylene production, sometimes it is desirable to produce both. In this embodiment, some portion of the mixed n-butenes feed 50 is heated at 52 and 54 and isomerized at 56 to convert a portion of the 2-butene to 1-butene. The isomerization effluent is then superfractionated at 58 to separate a 1-butene overhead product 60 and a 2-butene rich stream 62 as a bottoms product. Dependent upon the extent of 1-butene product 60 desired as a fraction of the $C_4$ olefin stream, either some of the fresh feed is bypassed at 64 and/or more or less of the 2-butene rich bottoms stream 62 is recycled at 66 to the isomerization step 56 and reacted to form additional 1-butene. The remaining quantity 68 of the 2-butene rich stream is sent to the metathesis process of the present invention as shown in this FIG. 3 and as explained in connection with FIG. 2 for the production of propylene 24 and 1-hexene 46. Once again, the $C_4$, $C_5$ and $C_6$ streams 12, 14 and 26 are purged at 28, 30 and 32.

Figure 4:
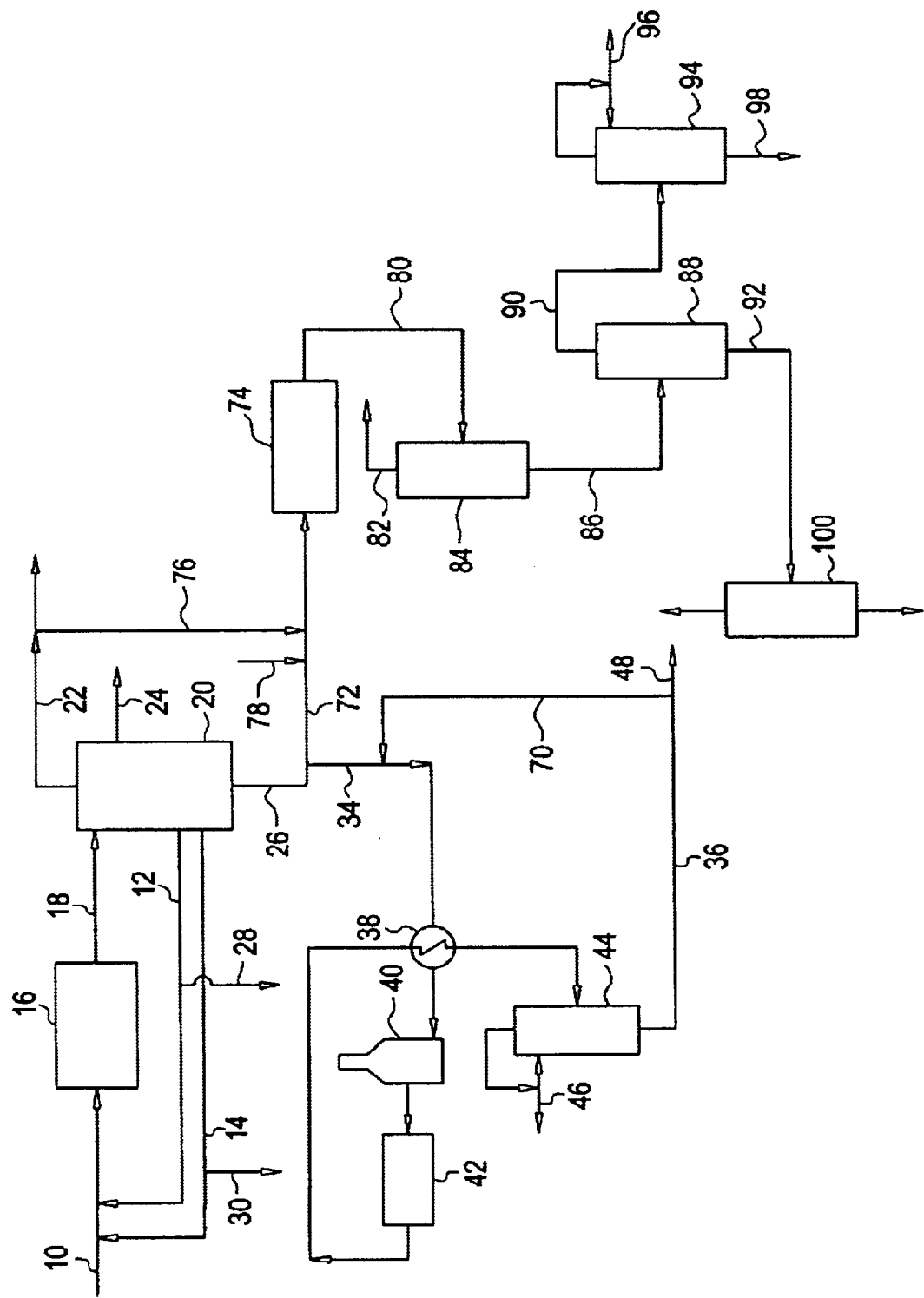
FIG. 4 is a flow diagram of an embodiment of the process with a reactive means for production of high purity 1-butene.

FIG. 4 shows an alternate means for the co-production of propylene, 1-butene, and 1-hexene. The mixed butenes feed 10 is sent to the process of the present invention as embodied in FIG. 1. For the same total mixed $C_4$ flow to the process as in FIG. 3, a larger flow is sent to the metathesis reactor 16 since none of the $C_4$'s have been separated to form 1-butene. From the conventional separator 20, a larger product $C_6$ stream 26 is produced as a result of the higher amount of the $C_4$ flow. The hexenes produced are principally 3-hexene. In this FIG. 4 embodiment, the portion 34 of the 3-hexene 26 is sent to an isomerization/superfactionation system to produce high purity 1-hexene 46 just as shown and described in connection with FIG. 2. At least a portion of the bottoms 36 from the tower 44, which is a mixed 2- and 3-hexene stream, may be recycled at 70 to the isomerization/superfractionation system. The remainder is purged at 48. A portion 72 of the 3-hexene stream 26 is sent to a separate metathesis reactor where it is contacted with ethylene 76 produced in the first reaction step 16. The metathesis reactions at 74 occur as follows:

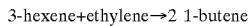

3-hexene+ethylene→2 1-butene

The extent of ethylene formation in the first metathesis reactor 16 is dependent upon the feed mixture and the extent of isomerization activity within this first metathesis reactor. If needed, additional ethylene 78 may be added. This metathesis reaction at 74 takes place using a catalyst system with low isomerization activity and under conditions that favor minimizing secondary reactions.

The effluent 80 from the metathesis reaction 74 now contains primarily 1-butene along with smaller quantities of unreacted ethylene, propylene, 2-butene, pentenes and unreacted hexene. The ethylene and $C_3$'s are removed in overhead 82 from tower 84 leaving the bottoms 86 containing the $C_4$+ components. The bottoms are then separated in tower 88 producing the $C_4$ overhead 90 and the $C_5$+ bottoms 92. The $C_4$ overhead 90 is separated in tower 94 into a relatively pure 1-butene overhead 96 and a bottoms 98 containing 2-butene and possibly some butane. If desired, the 2-butene could be recycled in the process. The high purity 1-butene stream 96 is consistent with purity requirements for polymerization reactor feed. The bottoms 92 are separated in tower 100 into a $C_5$ overhead and a $C_6$ bottoms which also may be recycled in the process. The cost in both capital and energy for the extensive isomerization and superfractionation system is avoided since instead of a moderately low 1-butene concentration in the $C_4$ stream, stream 90 is essentially pure 1-butene.

In addition, the process that sends the greater amount of the $C_4$ olefin stream to metathesis and subsequently uses a small amount of ethylene in the metathesis of 3-hexene, produces a substantially greater amount of propylene compared to the process that splits the feed with some portion to isomerization to produce 1-butene and the other portion to metathesis to produce propylene and hexene. This can be illustrated in the following example.

A mixed butene feedstock is fed to the process of FIG. 3 or the process of FIG. 4. The material balances for these cases are shown below.

FIG. 3 Case

| Feed mol/hr | Feed to Metathesis | Feed to $C_4$ Isomerization | Combined Feed |
|---|---|---|---|
| 1-butene | 670 | 331 | 1001 |
| 2-butene | 518 | 37 | 555 |
| Total Butenes | 1189 | 367 | 1556 |
| Ethylene | 0 | 0 | |
| Total Olefins | 1189 | 367 | 1556 |
| Inerts | 554 | 105 | 659 |
| Total feed, mols/hr | 1743 | 472 | 2215 |

| Products, mol/hr | |
|---|---|
| Ethylene | 16 |
| Propylene | 509 |
| 1-Butene | 356 |
| 1-Hexene | 239 |
| Olefin in Purges | 436 |
| Inerts | 659 |

FIG. 4 Case

| Feed mol/hr | Feed to Metathesis | Feed to $C_4$ Isomerization | Combined Feed |
|---|---|---|---|
| 1-butene | 1001 | 0 | 1001 |
| 2-butene | 555 | 0 | 555 |
| Total Butenes | 1556 | 0 | 1556 |
| Ethylene | 260 | 0 | 260 |
| Total Olefins | 1816 | | 1816 |
| Inerts | 659 | 0 | 659 |
| Total feed, mols/hr | 2475 | 0 | 2475 |

| Products, mol/hr | |
|---|---|
| Ethylene | 19 |
| Propylene | 1044 |
| 1-Butene | 357 |
| 1-Hexene | 238 |
| Olefin in Purges | 158 |
| Inerts | 659 |

| Product Olefin Selectivity % (purge olefins removed) | | | | |
|---|---|---|---|---|
| | Ethylene | Propylene | 1-Butene | 1-Hexene |
| FIG. 3 | 1.4 | 45.4 | 31.8 | 21.3 |
| FIG. 4 | 1.1 | 63.0 | 21.5 | 14.4 |

The basis of this comparison is an equivalent production of 1-butene and 1-hexene comonomer for linear low density polyethylene production starting with the same quantity of $C_4$ olefins. For the FIG. 3 case, approximately 45% of the feedstock olefins ($C_4$'s) are reacted to propylene. The purge of $C_4$ olefins is relatively high (436 mols/hr or 28% of the total $C_4$ olefins in the feed). This significant purge of olefins is in part due to the difficulties in separating the $C_4$ olefins from the $C_4$ paraffins in a $C_4$ only stream.

For the FIG. 4 case, approximately 63% of the feedstock olefins ($C_2$ and $C_4$) are reacted to propylene. Note that the ethylene is not reacting with butenes as is the case in conventional metathesis but reacts with the product 3-hexene. In this case, a larger total number of the $C_4$ olefins in the feed are reacted representing a higher efficiency processing case. In simple terms, the comparison can be stated as follows:

By feeding 260 mols/hr of ethylene, an additional 278 mols of butenes can be reacted (less $C_4$ olefin loss in the purge. This results in an increase of 535 mols/hr of propylene. Thus by utilizing a metathesis reaction between ethylene and 3-hexene following the metathesis of $C_4$ olefins without ethylene), the utilization of the $C_4$ olefins in the feed is increased, propylene is produced at an effective 99% selectivity, and high capital cost and energy cost superfractionation of butenes and butanes is avoided.

As an option to the flow scheme shown in FIG. 4, a divided wall distillation tower may be used to replace towers 84 and 88.

The process of FIG. 1 is used to react the mixed butenes and form the products ethylene, propylene, and 3-hexene. A further embodiment is shown in FIG. 5 wherein the 3-hexene stream 26, the $C_4$ purge stream 28 and the $C_5$ purge stream 30 are combined with hydrogen 132 and hydrogenated at 134. The hydrogenation effluent 136 is then recycled and fed to the cracking heaters 138 along with the primary cracker feed 140. The product 142 from the cracking heaters 138 is processed at 144 to remove $H_2$, $CH_4$, $C_2$'s and $C_3$'s as well as the $C_5$'s, $C_6$'s and heavier. The $C_4$'s 146 are combined with hydrogen 148 for hydrogenating the butadiene at 150. The isobutylenes are then removed at 152. A preferred method for processing the effluent 142 from the cracking heaters is described later in conjunction with FIG. 6. The processed feed is now an essentially pure normal butene stream which comprises the feed 10 to the metathesis process. The following table shows the yield patterns from pyrolysis of the normal $C_4$, $C_5$, and $C_6$ paraffin streams. The yield of paraffins assumes the olefins produced by either the steam cracker ($C_4$-s) or metathesis are hydrogenated prior to recycle. Also, the total $C_2/C_3/C_4$ olefins listed includes the 1,3 butadiene.

Pyrolysis Yields, wt %

|  | n-$C_4$s | n-$C_5$s | n-$C_6$s |
|---|---|---|---|
| $CH_4$ | 18.3 | 15.91 | 12.81 |
| $C_2H_4$ | 44.86 | 47.61 | 44.46 |
| $C_3H_6$ | 15.7 | 17.54 | 18.07 |
| 1,3 $C_4H_6$ | 3.43 | 4.85 | 4.97 |
| BUTENES | 2.12 | 2.95 | 4.05 |
| BUTANES | 5 | 0.02 | 0.02 |
| TOTAL $C_2/C_3/C_4$ OLEFINS | 66.11 | 72.95 | 71.55 |
| OLEFINS/$CH_4$ | 3.61 | 4.59 | 5.59 |

As can be seen, the total olefins produced from $C_5$ and $C_6$ paraffins are higher than from the $C_4$ paraffins. A common measure of feedstock performance is the ratio of olefins which are valuable products to methane which is commonly used as fuel. As can be seen, the $C_6$ stream is a better feedstock in terms of producing a higher ratio of valuable products to fuel. It is important to note that $C_5$ and $C_6$ streams directly from the cracker are not nearly as preferred as the $C_5$ and $C_6$ feedstocks from metathesis for recycle since they contain cyclo olefins and paraffins (both streams) and additionally benzene ($C_6$ stream). These reduce ethylene and propylene potential dramatically. The $C_5$ and $C_6$ streams from metathesis are linear and result in excellent feedstocks once hydrogenated.

The option of processing a normal $C_4$ stream through metathesis and recycle cracking the excess $C_5$ and $C_6$ streams produces significantly more olefins if one considers that propylene is produced from the metathesis reaction. This can be illustrated by the following example. A feed consisting of 100 pounds of the $C_4$ olefin mix is hydrogenated and recycle cracked. The products include 47.3 pounds of ethylene and 16.5 pounds of propylene. The test Run 148 from the previous table had a fresh normal butene feed consisting a 2/1 mixture of 2 butene to 1 butene. With recycle pentenes, the same 100 pounds of $C_4$'s produce 2 pounds of ethylene and 38 pounds of propylene. If the $C_5$ and $C_6$ olefin streams are then hydrogenated and recycle cracked, they produce considerably more ethylene and propylene. The combination of metathesis and cracking is significantly better than hydrogenating and recycle cracking the $C_4$ olefins.

| Yield as wt % feed | Pyrolysis of $C_4$ Olefins (as N-Butane) | Metathesis of $C_4$ Olefins | Metathesis of $C_4$ Olefins plus yield from Pyrolysis of $C_5/C_6$ Olefins (as paraffins) |
|---|---|---|---|
| Ethylene | 47.3 | 2 | 2 + 27.4 = 29.4 |
| Propylene | 16.5 | 38 | 38 + 10.5 = 48.5 |
| Pentenes | 0 | 36.3 | 0 |
| Hexenes | 0 | 22.7 | 0 |
| Other | 36.3 | 1 | 22.1 |
| Total $C_2/C_3$ Olefins | 63.8 | 40 | 77.9 |

Figure 6:
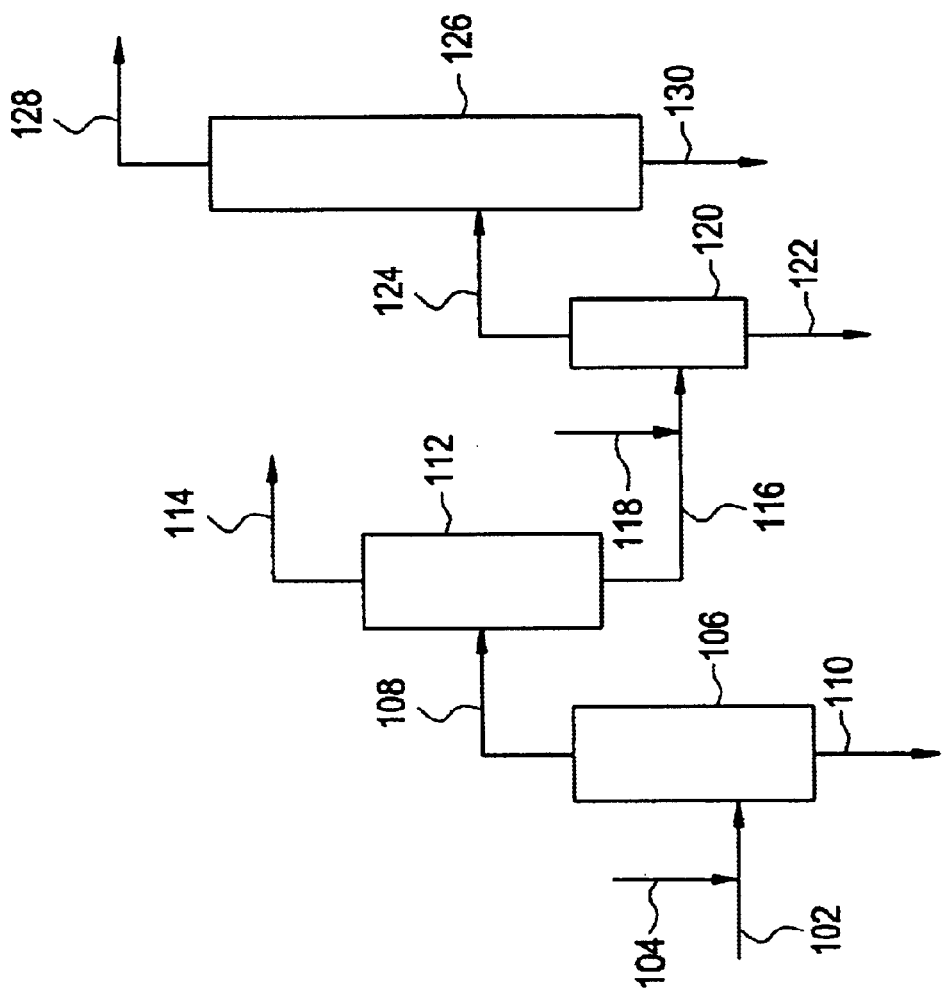
FIG. 6 is a flow diagram of a process according to the present invention for treating a $C_3$ to $C_6$ cut for propylene production by the auto-metathesis of 2-butene.

The process of the present invention employs a mixed n-butene feed which is obtained from a $C_3$ to $C_6$ hydrocarbon cut from a cracking process, such as steam or fluid catalytic cracking. Illustrated in FIG. 6 is a preferred example of a system for processing such a $C_3$ to $C_6$ cut to obtain that mixed n-butene feed. In this system, the $C_3$ to $C_6$ feed mixture 102 contains primarily propane, propylene, butane, 1-butene, 2-butene, isobutene, butadiene and acetylenic hydrocarbons as well as $C_5$ and $C_6$ components. This mixture 102 is fed along with hydrogen 104 to a catalytic distillation column 106 containing hydrogenation catalyst and distillation internals. This column 106 is preferably operated as a debutanizer, although it could be operated as a depentanizer, for substantial hydrogenation of the acetylenic and diene components with little hydrogenation losses of butenes and propylene. The net overhead 106 contains only very small quantities of acetylenes and dienes and the loss of olefins to paraffins is minimized. Essentially all of the methyl acetylene, propadiene, vinyl acetylene, ethyl acetylene and butadiene are hydrogenated to their respective olefins. The overhead 108 contains propane, propylene, butene-1, butene-2, isobutylene and some of the $C_5$ components. The bottoms 110 basically contain the remaining $C_5$ and the heavier components which are further processed as desired. The overhead 106 is fed to a de-propanizer tower 112 where the propane and propylene are removed overhead at 114 and sent for separation and recovery of propane and propylene. The bottoms 116 contain the $C_4$ and heavier components including the butenes. Any residual methyl acetylene and propadiene which may have been carried over from the tower 106 may be hydrogenated in this tower 112.

The bottoms 116 from column 112 are $C_4$'s if column 106 is a debutanizer or a mix of $C_4$ and $C_5$ if column 106 is a depentanizer. A small amount of hydrogen 118 and this mixed stream 116 is fed to a catalyst column 120 which serves to hydrogenate any residual butadiene which may have broken through in the overhead from column 106 to keep the selectivity high. The low level of hydrogen and a low activity catalyst are selective for hydrogenating only the acetylenes and dienes.

The bottoms 122 from the column 120 contains any residual $C_5$ and heavier components. This will prevent their return to the process and control the $C_5$ content in the ultimate feed to the metathesis unit which will increase catalyst on stream time. By incorporation of these towers, heavier $C_5$ compounds such a cyclopentenes that are difficult to process in metathesis are eliminated. Some of the lighter $C_5$ components can be allowed to pass overhead. The extent to which that is done depends upon the extent of iso $C_5$ compounds desired in the metathesis feed which ultimately impacts the product purity. The ability to do the bulk of the hydrogenation in column 106 and cleanup in columns 112 and 120 using very controlled amounts of hydrogen keeps selectivity of butadienes to butenes high and avoids losses to butanes.

The overhead 124 from the column 120 is the $C_4$ components and is primarily a mixture of isobutene, 1-butene and 2-butene. This mixture 124 is fed to the catalytic fractionation column 126 which has catalyst beds located above the feed in the rectifying section alternating with distillation trays or packing. Distillation trays or packing are also located in the stripping section of this column 126. This column 126 is a hydroisomerization tower and a deisobutylenizer. The hydrogen which was added upstream of column 120 or fresh hydrogen which is added will first hydrogenate the butadiene. Any remaining hydrogen will act as a co-feed for the hydroisomerization. The intent is not to hydrogenate any further so the least amount of hydrogen required is chosen. The exact quantity will depend upon the amount of butadiene that is carried over and the exact choice of catalyst in columns 120 and 126. The advantage of column 126 is that 1-butene may be isomerized to 2-butene to any extent desired. By reacting 1-butene to 2-butene, the losses of 1-butene in the overhead 128 are minimized and the butene in the bottoms 130 for feed to the metathesis reactor is maximized.

One of the functions of the column 126 is to remove the isobutene overhead at 128 with the isobutene having a low 1-butene content. The 1-butene boils at a lower temperature than the 2-butene and thus will tend to rise in the fractionation column 126. The isobutene is the lowest boiling of the mixture and will tend to go overhead. The 2-butene is fractionated from the mixture and is removed as the bottom product 130. As the 1-butene rises through the rectifying section in contact with the hydrogenation catalyst and in the presence of the extremely low quantities of hydrogen, at least some of the 1-butene is isomerized to 2-butene which then moves down the column. Moving up in the column, the distillation fractionation of the 1-butene increases due to volatility but it is subsequently isomerized to 2-butene. The equilibrium driving force for the isomerization of the 1-butene increases as the 1-butene concentration increases by fractionation and the product 2-butene is continually removed from the equilibrium zone as it moves toward the bottom of the tower. The net result is that a large portion of the 1-butene may be hydroisomerized to 2-butene. This reduces 1-butene losses in the overhead 128. Although the process as described for processing the feed to obtain the essentially pure metathesis feed is preferred, alternate processes can be used. As one example, the isobutylene may be removed by reaction with methanol to form MTBE.

What is claimed is:

1. A process for the conversion of a n-butene feed containing both 1-butene and 2-butene to propylene comprising the steps of:
   (a) passing said n-butene feed and a 2-pentene feed into an autometathesis reactor in contact with a methathesis catalyst whereby said 1-butene and 2-butane react to form propylene and 2-pentene and said 2-pentene stream reacts with 1-butene to form additional propylene and 3-hexene;
   (b) separating the effluent from said autometathesis reactor into a propylene product stream, an unreacted n-butene stream, a 2-pentene stream and a product 3-hexene stream; and
   (c) recycling at least a portion of said separated 2-pentene stream as said 2-pentene feed to said autometathesis reactor;
   wherein said n-butene feed is obtained from a pyrolysis cracking process and wherein only a portion of said separated 2-pentene stream is recycled leaving an unrecycled portion comprising the further steps of hydrogenating said unrecycled portion of said 2-pentene stream and at least a portion of said product 3-hexene stream and then recycling these hydrogenated streams back to the pyrolysis cracking process.

2. A process as recited in claim 1 wherein said metathesis catalyst is selected from the group consisting of the oxides of Group VI B and Group VII B metals.

3. A process as recited in claim 2 wherein said catalyst is on a support selected from the group consisting of silica, alumina, zirconia and zeolite.

4. A process as recited in claim 2 wherein said catalyst comprises tungsten oxide on a silica support.

5. A process as recited in claim 2 wherein said metathesis reaction is carried out at a temperature in the range of 50 to 450° C. and a pressure from 2 to 40 atmospheres.

6. A process as recited in claim 5 wherein said temperature is in the range of 300 to 400° C. and said pressure is from 5 to 15 atmospheres.

7. A process as recited in claim 1 and comprising the further steps of heating at least a portion of said 3-hexene stream to an isomerization temperature and passing said heated 3-hexene stream in contact with an isomerization catalyst whereby 3-hexene is isomerized to form a mixture, of 1-hexene, 2-hexene and 3-hexene and separating said 1-hexene as product and recycling said 2-hexene and 3-hexene back in contact with said isomerization catalyst.

8. A process as recited in claim 7 wherein said metathesis catalyst is selected from the group consisting of the oxides of Group VI B and Group VII B metals.

9. A process as recited in claim 8 wherein said metathesis catalyst is on a support selected from the group consisting of silica, alumina, zirconia and zeolite.

10. A process as recited in claim 7 wherein said metathesis catalyst comprises tungsten oxide on a silica support.

11. A process as recited in claim 7 wherein said isomerization catalyst is a basic metal oxide.

12. A process as recited in claim 11 wherein said isomerization catalyst is selected from the group consisting of MgO and CaO and mixtures thereof.

13. A process as recited in claim 7 wherein said metathesis reaction is carried out at a metathesis temperature in the range of 50 to 450° C. and a pressure from 2 to 40 atmospheres.

14. A process as recited in claim 13 wherein said metathesis temperature is in the range of 300 to 400° C. and said pressure is from 5 to 15 atmospheres.

15. A process as recited in claim 7 wherein said isomerization temperature is in the range of 300 to 450° C. and the pressure of said isomerization is in the range of 1 to 20 atmospheres.

16. A process as recited in claim 15 wherein said isomerization pressure is in the range of 3 to 10 atmospheres.

17. A process as recited in claim 11 wherein said metathesis catalyst is selected from the group consisting of the oxides of Group VI B and Group VII B metals.

18. A process as recited in claim 17 wherein said metathesis catalyst is on a support selected from the group consisting of silica, alumina, zirconia and zeolite.

19. A process as recited in claim 17 wherein said metathesis catalyst comprises tungsten oxide on a silica support.

20. A process as recited in claim 17 wherein said metathesis reaction is carried out at a temperature in the range of 50 to 450° C. and a pressure from 2 to 40 atmospheres.

21. A process as recited in claim 20 wherein said temperature is in the range of 300 to 400° C. and said pressure is from 5 to 15 atmospheres.

22. A process as recited in claim 1 comprising the further steps of reacting at least a portion of the product 3-hexene stream with ethylene under metathesis conditions where the isomerization of 3-hexene is limited thereby producing a reaction product containing 1-butene and separating said reaction product and recovering 1-butene as a 1-butene stream.

23. A process as recited in claim 22 wherein said metathesis catalyst is selected from the group consisting of the oxides of Group VI B and Group VII B metals.

24. A process as recited in claim 23 wherein said catalyst is on a support selected from the group consisting of silica, alumina, zirconia and zeolite.

25. A process as recited in claim 23 wherein said catalyst comprises tungsten oxide on a silica support.

26. A process as recited in claim 23 wherein said metathesis reaction is carried out at a temperature in the range of 50 to 450° C. and a pressure from 2 to 40 atmospheres.

27. A process as recited in claim 26 wherein said temperature is in the range of 300 to 400° C. and said pressure is from 5 to 15 atmospheres.

28. A process of claim 22 where the separation of said reaction products is performed in a divided wall column.

29. A process as recited in claim 1 wherein sad n-butene feed is obtained from a pyrolysis cracking process effluent containing butadiene and isobutylene and wherein said pyrolysis cracking process effluent is processed by catalytic distillation and hydroisomerization for the removal of butadiene and isobutylene.

30. A process as recited in claim 1 wherein a 1-butene product is also obtained comprising the further steps of isomerizing said n-butene feed containing 1-butene and 2-butene in the presence of an isomerization catalyst and thereby converting a portion of said 2-butene to 1-butene and fractionating the effluent from said isomerization to recover a 1-butene product overhead and a 2-butene rich bottom stream and feeding at least a portion of said 2-butene rich bottom stream as said n-butene feed to said autometathesis reactor.

31. A process as recited in claim 30 wherein said metathesis catalyst is selected from the group consisting of the oxides of Group VI B and Group VII B metals.

32. A process as recited in claim 31 wherein said metathesis catalyst is on a support selected from the group consisting of silica, alumina, zirconia and zeolite.

33. A process as recited in claim 31 wherein said metathesis catalyst comprises tungsten oxide on a silica support.

34. A process as recited in claim 31 wherein said metathesis reaction is carried out at a temperature in the range of 50 to 450° C. and a pressure from 2 to 40 atmospheres.

35. A process as recited in claim 34 wherein said temperature is in the range of 300 to 400° C. and said pressure is from 5 to 15 atmospheres.

36. A process as recited in claim 32 wherein said isomerization catalyst is a basic metal oxide.

37. A process as recited in claim 36 wherein said isomerization catalyst is selected from the group consisting of MgO and CaO and mixtures thereof.

38. A process for the conversion of a n-butene feed containing both 1-butene and 2-butene to propylene comprising the steps of:

(a) passing said n-butene feed and a 2-pentene feed into an autometathesis reactor in contact with a methathesis catalyst whereby said 1-butene and 2-butene react to form propylene and 2-pentene and said 2-pentene stream reacts with 1-butene to form additional propylene and 3-hexene;

(b) separating the effluent from said autometathesis reactor into a propylene product stream, an unreacted n-butene stream, a 2-pentene stream and a product 3-hexene stream;

(c) recycling at least a portion of said separated 2-pentene stream as said 2-pentene feed to said autometathesis reactor;

(d) reacting at least a portion of the product 3-hexene stream with ethylene under metathesis conditions where the isomerization of 3-hexene is limited thereby producing a reaction product containing 1-butene; and (e) separating said reaction product and recovering 1-butene as a 1-butene stream.

39. A process as recited in claim 38 wherein said metathesis catalyst is selected from the group consisting of the oxides of Group VI B and Group VII B metals.

40. A process as recited in claim 39 wherein said catalyst is on a support selected from the group consisting of silica, alumina, zirconia and zeolite.

41. A process as recited in claim 39 wherein said catalyst comprises tungsten oxide on a silica support.

42. A process as recited in claim 39 wherein said metathesis reaction is carried out at a temperature in the range of 50 to 450° C. and a pressure from 2 to 40 atmospheres.

43. A process as recited in claim 42 wherein said temperature is in the range of 300 to 400° C. and said pressure is from 5 to 15 atmospheres.

44. A process of claim 38 where the separation of said reaction products is performed in a divided wall column.

* * * * *

UNITED STATES PATENT AND TRADEMARK OFFICE
CERTIFICATE OF CORRECTION

PATENT NO. : 6,777,582 B2
DATED : August 17, 2004
INVENTOR(S) : Gartside et al.

It is certified that error appears in the above-identified patent and that said Letters Patent is hereby corrected as shown below:

Column 14,
Line 12, delete "2-butane" and substitute -- 2-butene --.
Line 47, after "mixture" delete ",".

Column 15,
Line 47, delete "sad" and substitute -- said --.

Signed and Sealed this

Thirty-first Day of January, 2006

JON W. DUDAS
*Director of the United States Patent and Trademark Office*